US010369537B2

(12) United States Patent
Santos et al.

(10) Patent No.: US 10,369,537 B2
(45) Date of Patent: Aug. 6, 2019

(54) MULTI-NOZZLE SPRAY DRYER, METHOD FOR SCALE-UP OF SPRAY DRIED INHALATION POWDERS, MULTI-NOZZLE APPARATUS AND USE OF MULTIPLE NOZZLES IN A SPRAY DRYER

(71) Applicant: HOVIONE INTERNATIONAL LTD, Wanchai (CN)

(72) Inventors: José Luis Santos, Sintra (PT); Luis Olival, Lisbon (PT); Maria Palha, Lisbon (PT); Filipa Maia, Póvoa de Santa Iria (PT); Filipe Neves, Lisbon (PT)

(73) Assignee: Hovione Holding Limited, Wanchai (HK)

( * ) Notice: Subject to any disclaimer, the term of this patent is extended or adjusted under 35 U.S.C. 154(b) by 394 days.

(21) Appl. No.: 15/280,433

(22) Filed: Sep. 29, 2016

(65) Prior Publication Data

US 2017/0014789 A1    Jan. 19, 2017

Related U.S. Application Data

(63) Continuation of application No. PCT/GB2015/050960, filed on Mar. 30, 2015.

(30) Foreign Application Priority Data

Mar. 31, 2014    (PT) .......................................... 107567

(51) Int. Cl.
    *B01J 2/04*    (2006.01)
    *B01D 1/18*    (2006.01)
    *A61K 9/16*    (2006.01)

(52) U.S. Cl.
    CPC .............. *B01J 2/04* (2013.01); *A61K 9/1682* (2013.01); *B01D 1/18* (2013.01)

(58) Field of Classification Search
    None
    See application file for complete search history.

(56) References Cited

U.S. PATENT DOCUMENTS

| 6,845,571 B1 | 1/2005 | Schwarz et al. |
| 8,524,279 B2 | 9/2013 | Snyder et al. |
| 2002/0007869 A1 | 1/2002 | Pui et al. |
| 2003/0180283 A1 | 9/2003 | Batycky et al. |
| 2004/0118007 A1 | 6/2004 | Chickering, III et al. |
| 2005/0013869 A1* | 1/2005 | Chaw .................. A61K 9/1647 424/501 |
| 2007/0148325 A1 | 6/2007 | Nishikawa et al. |

FOREIGN PATENT DOCUMENTS

| CN | 1625389 A | 6/2005 |
| CN | 1726076 A | 1/2006 |
| PT | 107567 | 3/2014 |
| WO | 03090893 A1 | 11/2003 |
| WO | 2015150761 A1 | 10/2015 |

OTHER PUBLICATIONS

Foreign Communication from a related application—Examination Report No. 1 of Australian Patent Application No. 2015242442, dated Mar. 14, 2018, 3 pages.
Foreign communication from a related application—Office Action of Chinese Patent Application No. 201580023072.0, dated Jul. 30, 2018, with translation, 13 pages.
Turton, Richard, et al., "The scale-up of spray coating processes for granular solids and tablets," Powder Technology, 2005, pp. 78-85, vol. 150, Elsevier B.V.
Green, Don W, et al., "Perry's Chemical Engineers' Handbook, Eighth Edition," 2008, 8 pages of cover, publishing information and table of contents, McGraw Hill Companies, Inc.
Foreign Communication from the Priority Application—International Search Report and Written Opinion of PCT/GB2015/050960 dated Jul. 17, 2015, 9 pages.
Foreign Communication from the Priority Application—International Preliminary Report on Patentability of PCT/GB2015/050960 dated Jun. 30, 2016, 9 pages.
Foreign communication from a related application—Examination Report No. 2 of Australian Application No. 2015242442, dated Jul. 18, 2018, 3 pages.
Foreign communication from a related application—Office Action of Japanese Patent Application No. 2016-560498, dated Jan. 8, 2019, with translation, 7 pages.
Foreign communication from a related application—Third Office Action of Australian Patent Application No. 2015242442, dated Feb. 26, 2019, 3 pages.

* cited by examiner

*Primary Examiner* — Mary Lynn F Theisen
(74) *Attorney, Agent, or Firm* — Conley Rose, P.C.; Rodney B. Carroll

(57) ABSTRACT

This present invention provides a spray dryer for use in preparing particles for inhalation, the spray dryer comprising a multi-nozzle apparatus comprising multiple single nozzles suitable for use in preparing inhalation powders and with a drying gas flow rate greater than about 80 kg/h. Also provided is a method for scaling-up a spray drying process for preparing particles for inhalation from a smaller scale spray dryer to a larger scale spray dryer, relative in size to each other, the method comprising the use in the larger scale spray dryer of a multi-nozzle apparatus comprising single nozzles suitable for use in preparing inhalation powders, wherein the number of nozzles in the larger spray dryer is determined by the ratio of the drying gas flow rate of the larger scale spray dryer to the drying gas flow rate of the smaller scale spray dryer. Also provided is a multi-nozzle apparatus produced from the method of the present invention, the multi-nozzle apparatus comprising multiple single nozzles suitable for use in preparing inhalation powders. Also provided is the use of multiple single nozzles suitable for use in preparing inhalation powders in a spray dryer with a drying gas flow rate greater than about 80 kg/h. The nozzles used in the present invention preferably prepare particles with a mean particle size less than about 5 microns.

20 Claims, 9 Drawing Sheets

MULTI-NOZZLE SPRAY DRYER, METHOD FOR SCALE-UP OF SPRAY DRIED INHALATION POWDERS, MULTI-NOZZLE APPARATUS AND USE OF MULTIPLE NOZZLES IN A SPRAY DRYER

CROSS-REFERENCE TO RELATED APPLICATIONS

The present application is a continuation of and claims priority to International Application No. PCT/GB2015/050960 filed Mar. 30, 2015, entitled "Multi-Nozzle Spray Dryer, Method for Scale-Up of Spray Dried Inhalation Powders, Multi-Nozzle Apparatus and Use of Multiple Nozzles in a Spray Dryer," which claims priority to Portuguese Application No. 107567 filed Mar. 31, 2014, which applications are incorporated by reference herein in their entirety.

FIELD OF INVENTION

The present invention is in the technical field of drying methods. More particularly, the present invention is in the technical field of spray drying applied particularly, but not exclusively, to active pharmaceutical ingredients (APIs), drug product intermediates and drug products intended for inhalation delivery. The active pharmaceutical ingredients (APIs), drug product intermediates and drug products may be organic compounds.

BACKGROUND OF THE INVENTION

The development of manufacturing processes for spray dried inhalation powders involves two challenging constraints: i) a very small particle size is required (with a mean diameter below 5 microns, typically below 3 microns); and ii) the particle size should not be allowed to increase during scale-up (despite the fact that the majority of powders spray dried for oral dosage delivery will tend to increase in particle size during scale-up). These constraints pose important challenges during development, as current off-the-shelf atomization systems lose efficiency when having to manage an increase in throughput upon scale-up. Such loss of efficiency makes necessary the use of a larger quantity of gas for atomization, which leads to distinct challenges depending on the type of atomization system used:

a) In the case of two-fluid external mixture nozzles (high consumers of atomization gas at low pressures), the flow rate of atomization gas may increase to such an extent that the drying chamber size and the rest of the process train may become under-dimensioned for the process (as the atomization gas flow rate requirement can increase, theoretically, to a demand of 30-50% of the total gas flow rate in the spray dryer).

b) For two-fluid internal mixture nozzles (low consumers of atomization gas at high pressures), an increase of atomization gas flow rate may promote such an increase in pressure drop in the nozzle that the pressure of the gas feed lines may often require very complex and expensive upgrades.

While such challenges might be overcome through engineering upgrades to the spray dryer process train, there remains an even more difficult challenge to address, since there is still the potential for the droplet size to be outside the intended range upon scale-up. It is not uncommon that the nozzle being applied at the smaller scale cannot be directly applied at the larger scale as its operating ranges are exceeded. Additionally, selecting a new nozzle is typically complex, time-consuming and expensive as extensive testing is required. Furthermore, there are no guarantees that such process development activities lead to a successful identification of an adequate candidate nozzle, as there are physical limitations to atomize large flow rates of liquid into small droplets within the target inhalation range. Hence, the current approach to controlling particle size within the inhalation range upon scale-up is limited by nozzle design (external or internal mixture, and nozzle model) and atomization gas flow rate. A different option for controlling particle size would be to decrease solids concentration in the feed mixture, but this is not a recommended approach as it negatively affects the process throughput and cycle time, and ultimately its feasibility from a process economics perspective.

The concept of using multi-nozzle atomization for combining high feed capacity with fine atomization for both pressure nozzles and two-fluid nozzles is known in the art [Green, D; Perry, R. "Perry's chemical engineers' handbook" (2008)]. The spray drying literature includes additional examples where multi-nozzle arrangements were used. For example, US 2002/0007869 discloses a multi-nozzle electrospraying method for the production of nanoparticles with high mass throughput.

WO 03/090893 discloses a process that uses a multi-nozzle apparatus to promote powder agglomeration with negligible product deposits on the walls, through reintroduction of the fines near the main spray plume.

In US 2007/0148325 a granulation method is disclosed for the production of fine aqueous particles using the necessary number of nozzles equivalent to those of conventional design.

A paper by Turton et al. [Turton, R; Cheng, X. "The scale-up of spray coating processes for granular solids and tablets"; Powder Technology 150 (2005) 78-85] discloses a spray coating process for granular solids and tablets that makes use of multiple nozzles to cover a wider area.

U.S. Pat. No. 8,524,279 discloses a process mostly intended for inhalation products that report the use of a multi-nozzle atomizer comprised of a central gas nozzle and a plurality of atomization nozzles around such central gas nozzle. The central gas nozzle is used to minimize spray plume interactions and to control the final powder characteristics, while the feed mixture is atomized in the atomization nozzles.

Whilst such examples mostly disclose multi-nozzle systems targeted for an increase in process throughput, and in some cases enabling the production of particles in the inhalable range, there remains a need in inhalation spray drying for a simple means of controlling particle size upon scale-up. The invention herein disclosed overcomes the shortcomings identified in the prior art, by using multiple low throughput off-the-shelf nozzles. The ratio between liquid and atomization gas flow rate can be maintained as constant in each nozzle across spray dryer scales, which leads to similar sized droplets across scales and eliminates the challenges faced during scale-up that were previously described. This enables a direct scale-up of the process since the operating conditions used in the smaller scale can be directly used in a larger scale spray dryer as each nozzle is geometrically the same across scales. In this way, the single scale-up action to be conducted will be to increase the number of nozzles to be used proportionally to the scale of the spray drying unit. Hence, the idea herein disclosed comprises two innovative concepts that overcome the limitations found in the art and expedites process development:

1) The ability to generate particles in the inhalable range (that is, characterized by a volumetric distribution with a mean geometric size below 5 microns), regardless of the required throughput; the high-throughput multi-nozzle systems that can be currently found in the art do not disclose such critical performance criterion, and
2) Meeting the target particle size range with the use of the same nozzle regardless of the scale (only the number of nozzles is being changed, not the model and type). The multi-nozzle systems that can be currently found available consider different variations/models when throughput is required to be increased above certain ranges.

Hence, the conventional pharmaceutical spray drying methods used in the production of inhalation powders are limited in terms of fulfillment of critical quality attributes (namely in what concerns the particle size distribution) when higher throughputs are required; the proposed concept is expected to overcome this limitation and, additionally, to expedite process development.

SUMMARY OF THE INVENTION

According to one aspect of the present invention, there is provided a spray dryer for use in preparing particles for inhalation, said spray dryer comprising a multi-nozzle apparatus comprising multiple single nozzles suitable for use in preparing inhalation powders, wherein the drying gas flow rate of the spray dryer is greater than about 80 kg/h.

According to another aspect of the present invention, there is provided method for scaling-up a spray drying process for preparing particles for inhalation from a smaller scale spray dryer to a larger scale spray dryer, relative in size to each other, said method comprising the use in the larger scale spray dryer of a multi-nozzle apparatus comprising single nozzles suitable for use in preparing inhalation powders, wherein the smaller scale spray dryer comprises a number m of nozzles and the larger scale spray dryer comprises a number n of nozzles, and wherein n is determined by the ratio of the drying gas flow rate of the larger scale spray dryer to the drying gas flow rate of the smaller scale spray dryer. The drying gas flow rate may be known as a nominal drying gas flow rate.

According to yet another aspect of the present invention, there is provided a multi-nozzle apparatus for use in a spray dryer, said multi-nozzle apparatus produced from the method described above, wherein the multi-nozzle apparatus comprises multiple single nozzles suitable for use in preparing inhalation powders.

According to a further aspect of the present invention, there is provided the use of multiple single nozzles suitable for use in preparing inhalation powders in a spray dryer, wherein the drying gas flow rate of the spray dryer is greater than about 80 kg/h.

The nozzles suitable for use in preparing particles for inhalation may be suitable for use in preparing particles for inhalation comprising active pharmaceutical ingredients, drug product intermediates or drug products, optionally organic active pharmaceutical ingredients, drug product intermediates or drug products. The particles for inhalation may have a mean particle size less than about 5 microns, preferably less than about 3 microns In the method of the present invention, n may be equal to the ratio of the drying gas flow rate of the larger scale spray dryer to the drying gas flow rate of the smaller scale spray dryer rounded up or down to a whole number. Furthermore, in the method of the present invention, m may be between 1 and 4, optionally m=1 or 2 or 3, and n may be between 2 and 16, preferably n=2 or 3 or 4 or 5 or 8 or 10 or 16. In fact, the number of single nozzles used in the spray dryer, multi-nozzle apparatus and use of the present invention may also be between 2 and 16, preferably n=2 or 3 or 4 or 5 or 8 or 10 or 16.

The drying gas flow rate of the smaller scale spray dryer may be from about 20 kg/h to about 120 kg/h, preferably from about 40 kg/h to about 80 kg/h, most preferably about 40 kg/h. The drying gas flow rate of the larger spray dryer may be larger than about 80 kg/h, in accordance with the spray dryer used in the first aspect of the present invention. Optionally, the drying gas flow rate of the spray dryer may be greater than about 120 kg/h or greater than about 150 kg/h. The drying gas flow rate of the spray dryer may be about 360 kg/h, about 650 kg/h or about 1250 kg/h.

The single nozzles used in the method and apparatus of the present invention may be two-fluid external or internal mixture nozzles preferably two-fluid external mixture nozzles. The liquid feed flow and atomization gas flow may be homogeneously distributed amongst the n single nozzles.

In some embodiments of the method of the present invention, the drying gas flow rate of the smaller scale spray dryer is about 80 kg/h and the drying gas flow rate of the larger spray dryer is about 360 kg/h and m=1 and n=4. Alternatively, the drying gas flow rate of the larger spray dryer is about 650 kg/h and m=1 and n=8.

The current invention considers an innovative concept where multiple nozzles are simultaneously used. Preferably, all nozzles are of the same type, and they can be chosen from any off-the-shelf commercially available nozzles typically used on spray dryers of small sizes (for example Size 1 (SD1), to which a nominal drying gas flow rate of approximately 80 kg/h corresponds). The new invention assures that the particle size distribution obtained by a single specific nozzle at the SD1 scale is the same obtained by the invention at larger scales (for example size 2 (SD2) or size 3 (SD3) scales to which a nominal drying gas flow rate of for example approximately 360 kg/h or approximately 650 kg/h of drying gas flow, corresponds respectively), without significant development work (that is, without requiring the type of nozzle to be changed and just via an increase in the number of nozzles used).

By "small spray dryer" or "small scale spray dryer" we mean spray dryers intended to be typically used in a laboratory setting or at pilot scale, having a typical nominal gas flow rate of 20 to 120 kg/h preferably of 40 to 80 kg/h. Examples of such spray dryers include but are not limited to BUCHI model B-290, with a typical nominal gas flow rate of about 20 to 40 kg/h, Niro Mobile Minor, with a typical nominal gas flow rate of about 40 to 120 kg/h, and Anhydro Spray Drying of SPX, with a typical nominal gas flow rate of about 35 to 150 kg/h.

By "large spray dryer" we mean spray dryers intended to be used in an industrial setting (even if the units are small production units) having typical nominal flow gas rate of >80 kg/h. Examples of such spray dryers include but are not limited to Niro spray dryers of size 2, 3 and 4 having typical nominal gas flow rate of about 360, 650 and 1250 kg/h (or upgraded units of size 1, prepared to handle larger drying gas flow rates) and Anhydro Spray Drying of SPX, with a typical nominal gas flow rate of about 400 to 2500 kg/h.

DETAILED DESCRIPTION OF THE INVENTION

Referring now to the invention in more detail, the spray dryer, method, apparatus and use of the present invention use multiple single nozzles of the type used in a smaller scale spray dryer for use in preparing inhalation powders in order to match the drying gas flow rate of a larger spray dryer. For example, for a single nozzle typical of a spray dryer (SD1) with a gas flow rate of approximately 80 kg/h 4 nozzles may be used for a spray dryer (SD2) with approximately 360 kg/h of drying gas, or 8 nozzles may be used for a spray dryer (SD3) with approximately 650 kg/h of drying gas—FIG. 1 shows a possible configuration of the resulting apparatus for the larger SD2 scale.

This means that the number of single nozzles used in the larger scale spray dryer is determined by the ratio of the drying gas flow rate of the larger scale spray dryer to the drying gas flow rate of the smaller scale spray dryer.

Figure 1:
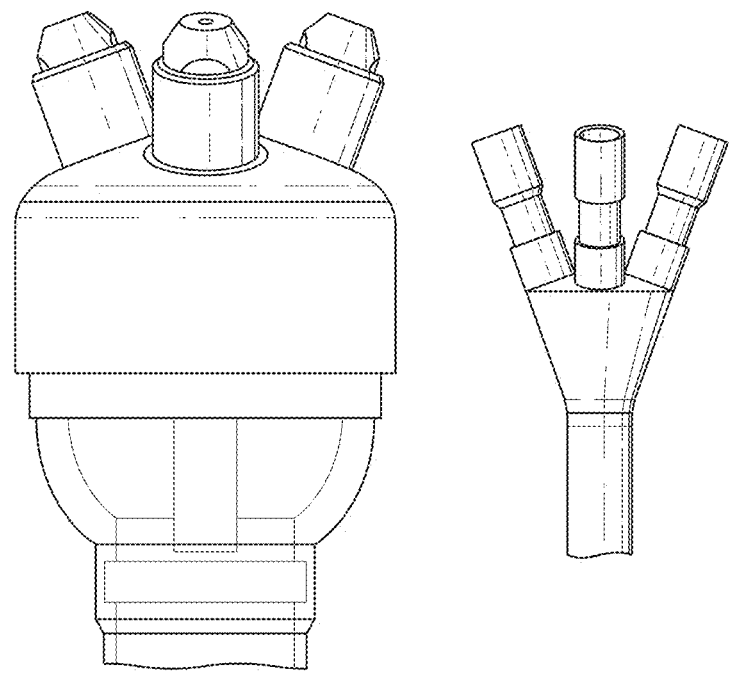
FIG. 1 is a representation of the multi-nozzle atomizer meant for a SD2 scale spray dryer (external view and view of the liquid circuit).
Figure 2:
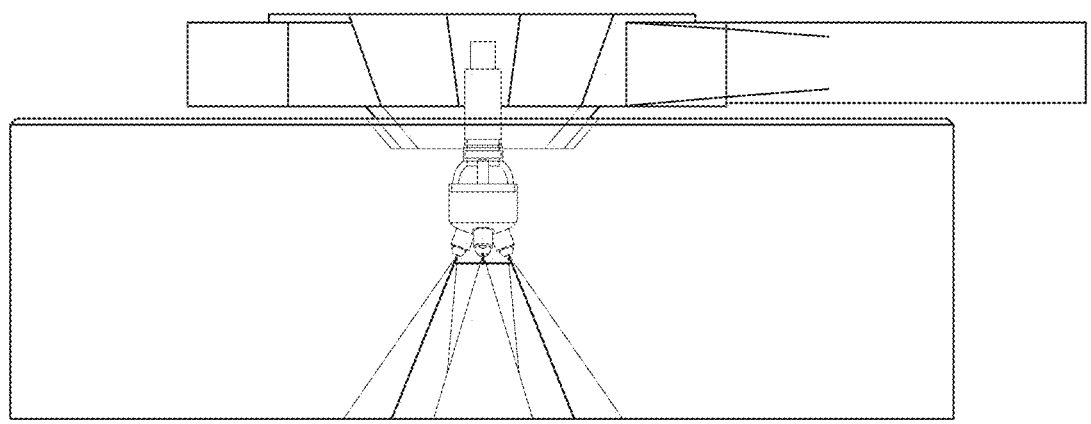
FIG. 2 is a side view illustration of the spray plumes of the multi-nozzle atomizer in a SD2 scale spray dryer.

In more detail, the present invention provides an apparatus with dimensions that enable the positioning of n single nozzles within the spray drying chambers, and that are the same as or similar to the dimensions of conventional off-the-shelf atomization systems, thereby avoiding expensive retrofitting of spray dryers or complex assembly procedures that are prone to human error—see FIG. 1 and FIG. 2. Hence the apparatus of the present invention may be used in an existing manufacturing plant in place of an existing atomization system.

The distribution of the liquid feed flow and atomization gas flow should be homogeneous amongst the n single nozzles as illustrated in FIG. 1 due to the symmetrical geometry of the apparatus. This enables a set of identical sprays and ensures droplet size is the same from one single nozzle to the other, and hence does not impact the final particle size distribution of the obtained powder.

Figure 3:
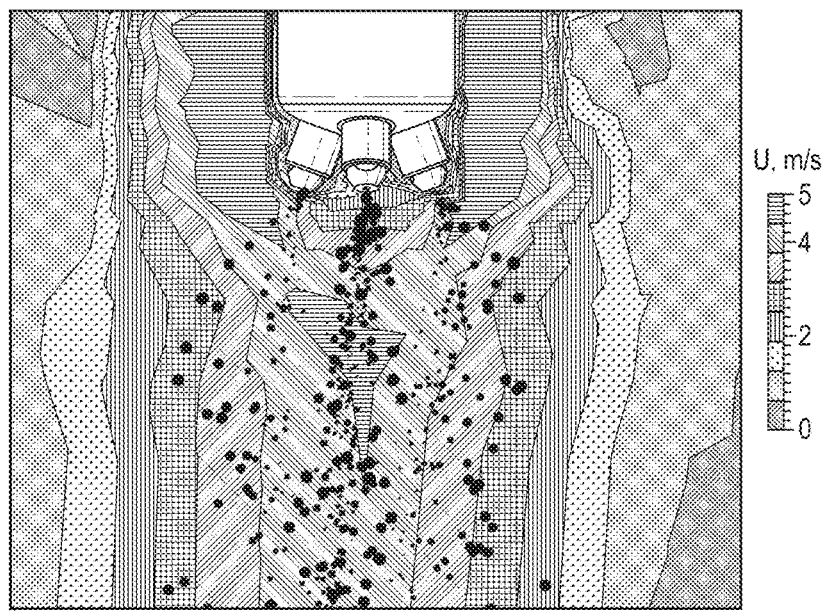
FIG. 3 shows results of a Computational Fluid Dynamics (CFD) simulation close to the nozzle.
Figure 4:
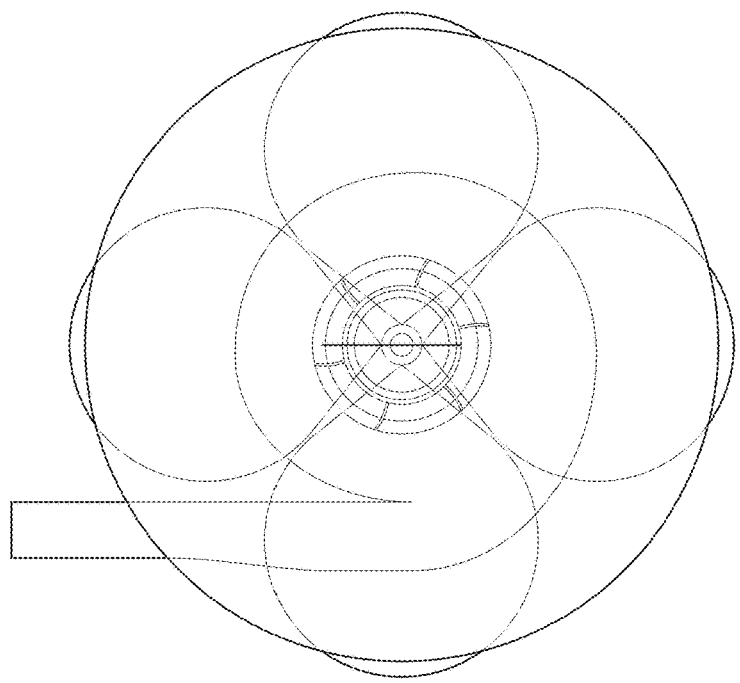
FIG. 4 is a top view illustration of the spray plumes of the multi-nozzle atomizer in a SD2 scale spray dryer.
Figure 5:
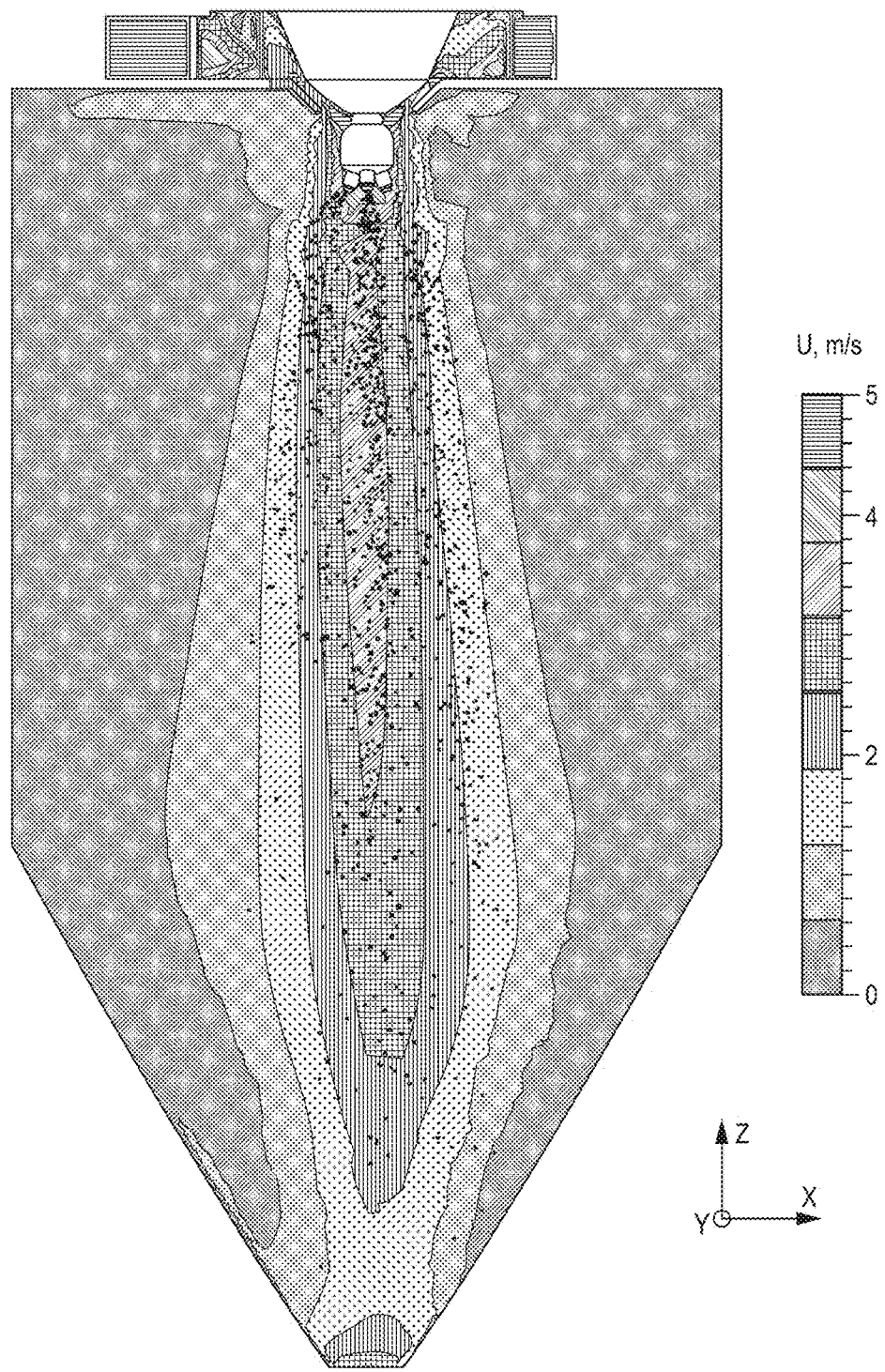
FIG. 5 shows results of a Computational Fluid Dynamics (CFD) simulation over the drying chamber.

The shape, size and positioning of the apparatus do not significantly impact the drying gas flow pattern within the spray drying chambers as shown in FIG. 3, which avoids any disruption to gas distribution and all the typical operational problems that derive from such. Moreover, the spray angles for each single nozzle (relative to each other) can be arranged such that no significant spray overlapping will occur (which could lead to droplet coalescence and, consequently, particle size increase)—see FIG. 4. As shown in FIG. 5, the spray angles for each single nozzle (relative to the chamber) can be arranged such that spray penetration will not cause the impact of droplets (nor of wet particles) on the walls of the equipment (which could lead to yield losses and product degradation). FIG. 5 also shows that the spray shape need not be impacted, thus avoiding the phenomena of secondary atomization (which could lead to droplet coalescence and break-up, with consequent impact on final particle size). Furthermore, other configurations of nozzles could readily be designed by the skilled person. For example the skilled person could arrange a set of four nozzles to direct spray in four different directions from a single point or could design two sets of two nozzles to direct spray in two different directions from two different points.

The advantages of the present invention include, without limitation, the simplification (to a great extent) of the scale-up of spray dried inhalation powders since no development (or minimal development) will be involved, as operating conditions from the smaller scale can be maintained approximately constant. Essentially, the single scale-up action required will be to increase the number of nozzles used. An additional benefit of the present invention is that it may be used as an enabling technology since, when moving to larger scale spray dryers (for example SD2 or larger), no scale-up methodologies are currently available in the art for inhalation powders. Similarly, no suitable nozzles are known for inhalation powders, since nozzle manufactures make no assurances of hitting the target particle size, reducing the applicability of the current technology.

In order that the invention may be more fully understood, the following examples are included by way of illustration only.

EXAMPLES

Example 1

Figure 6:
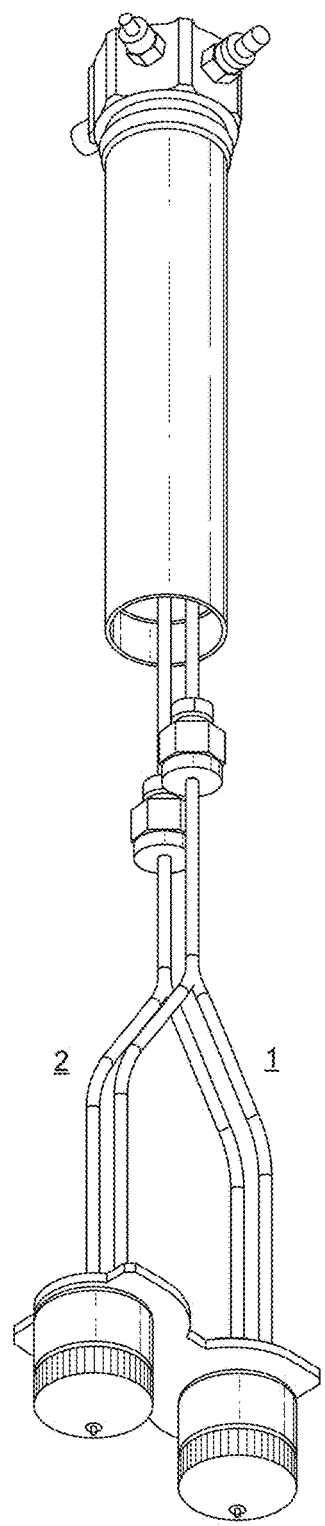
FIG. 6 shows the multi-nozzle system used in the laboratory experiments:
1—Solution feed
2—Gas feed
Figure 7:
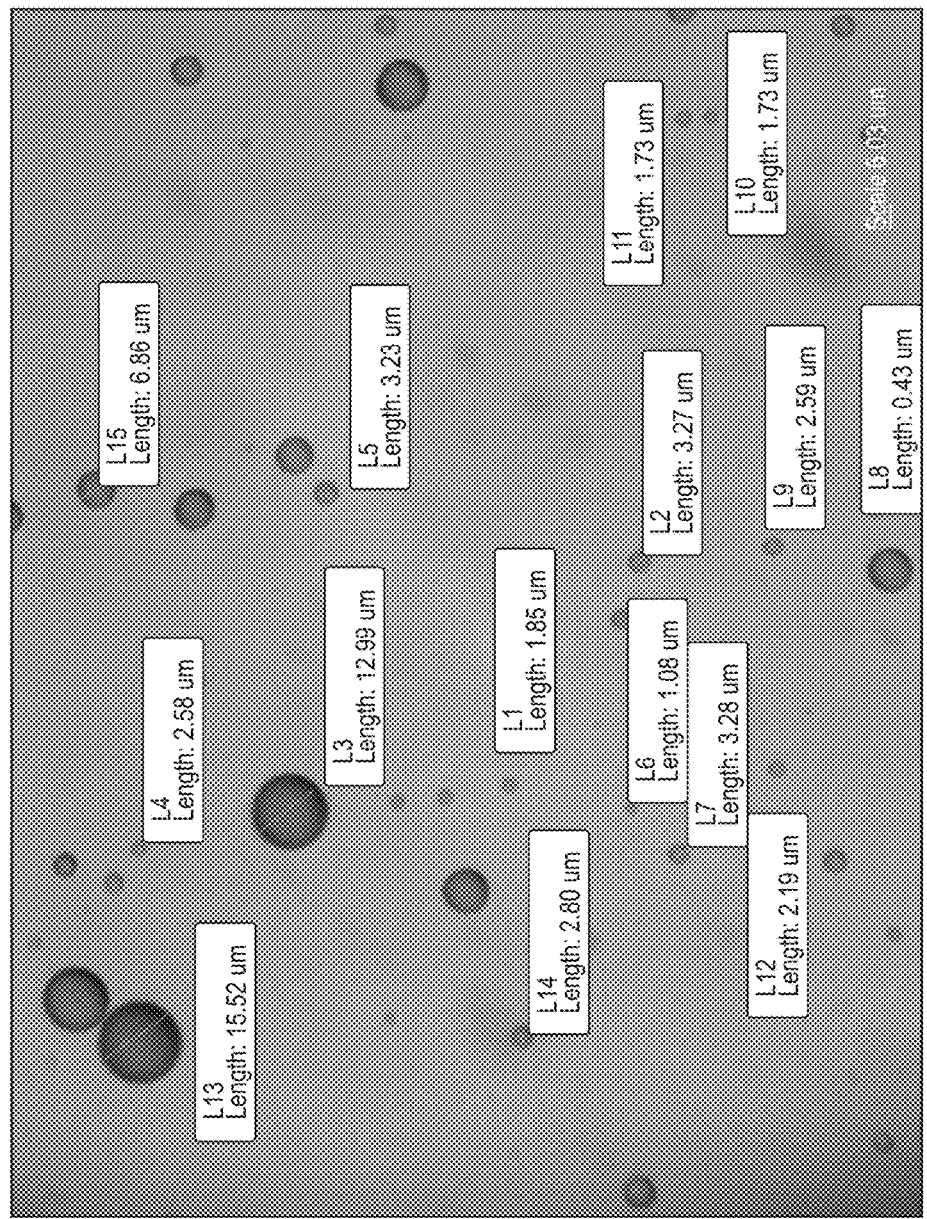
FIGS. 7 and 8 show optical microscopy images of the particles obtained in the laboratory experiments.
Figure 8:
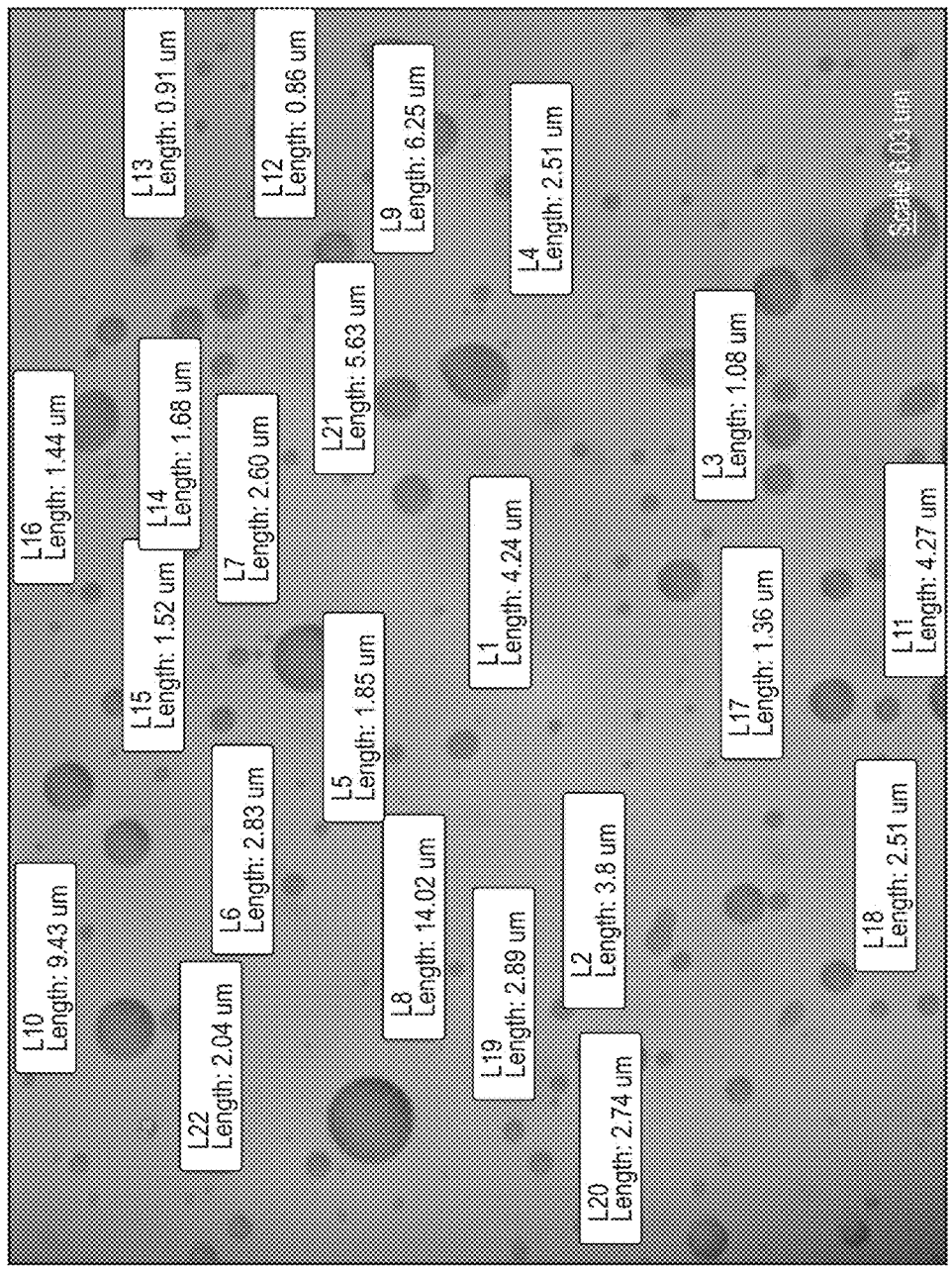
Figure 9:
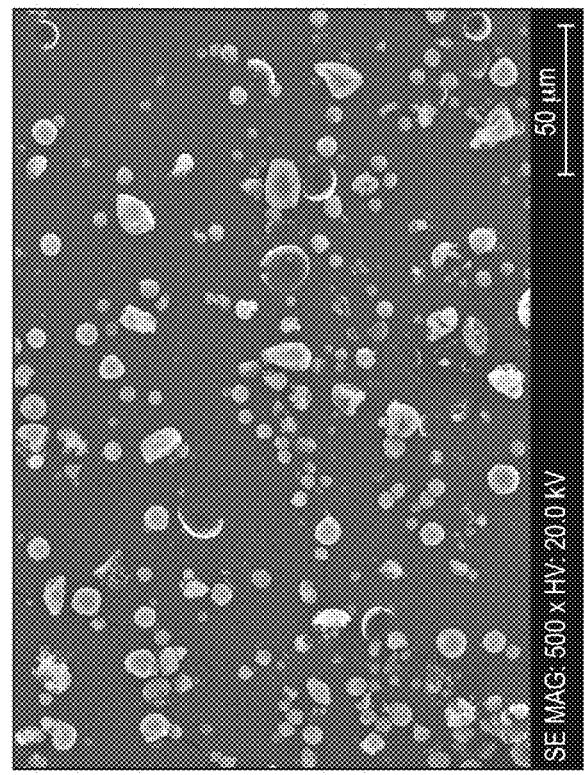
FIG. 9 shows scanning electron microscope images of the particles obtained in the SD1 unit experiments (left side—multi-nozzle atomizer operating with 2 nozzles and right side—multi-nozzle atomizer operating with 1 nozzle).
Figure 9:
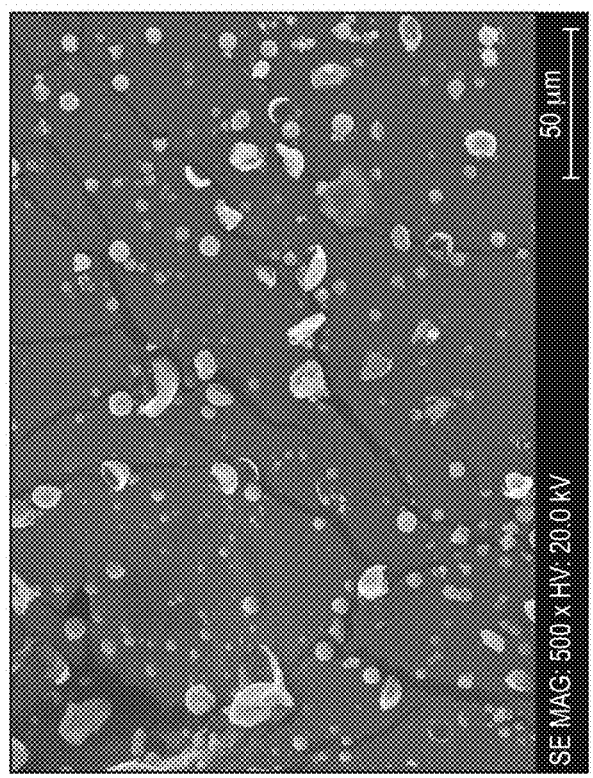
Figure 10:
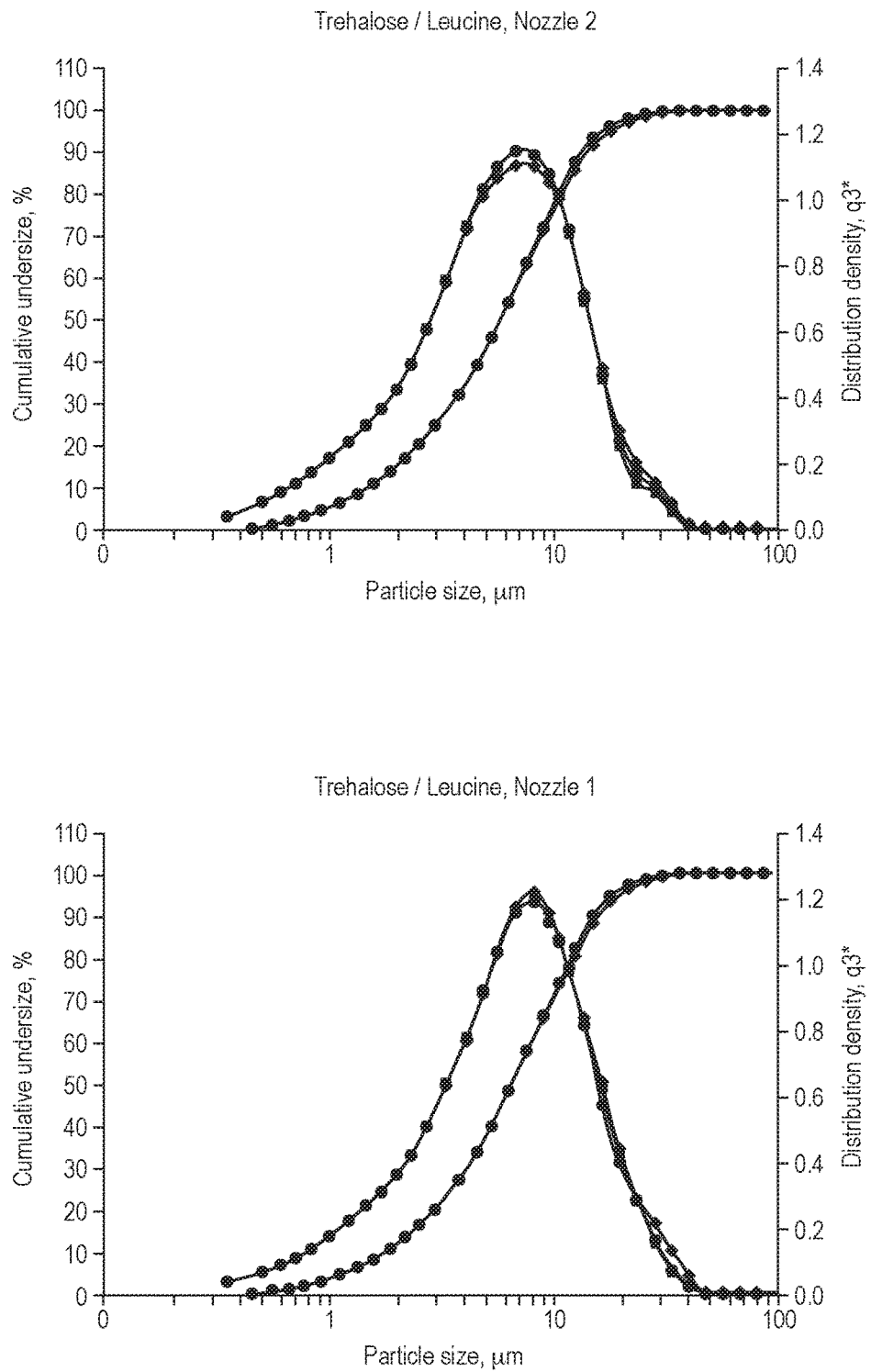
FIG. 10 shows the particle size distribution of the particles obtained in the SD1 unit experiments (left side—multi-nozzle atomizer operating with 2 nozzles and right side—multi-nozzle atomizer operating with 1 nozzle).
Figure 11:
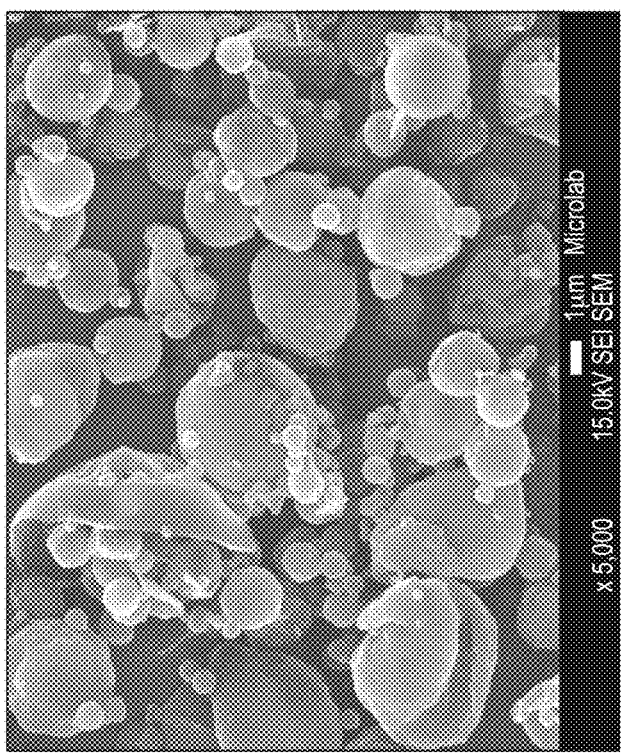
FIG. 11 shows scanning electron microscope images of the particles obtained in the commercial scale spray dryer experiment.
Figure 11:
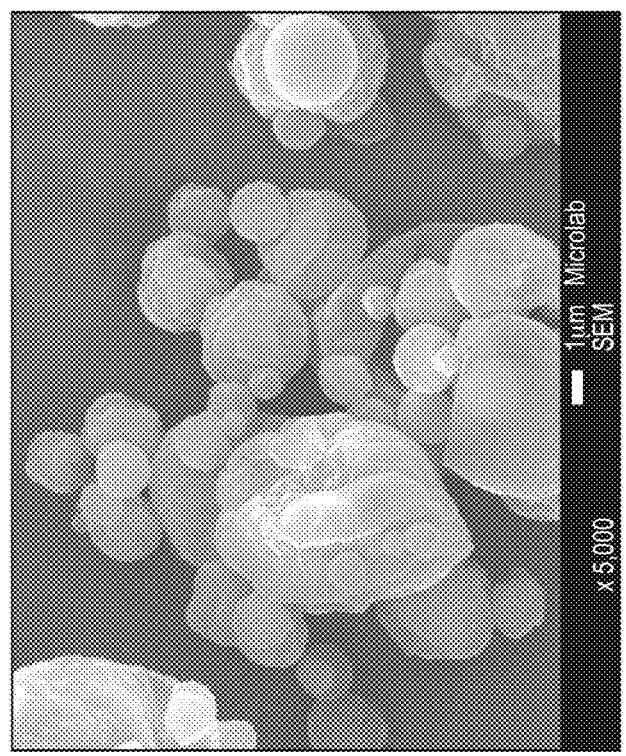

This example demonstrates the proof-of-concept, by considering a scaled-down version (shown in FIG. 6) of the invention.

A feed mixture was prepared by dissolving 1.2 g of lysine and 4.8 g of trehalose in 234 g of water (total solids concentration approximately 2.5% w/w). This excipient system is known to yield amorphous powders, where particle size is more sensitive to variations of the atomization conditions. Therefore, this excipient system is ideal for the current proof-of-concept.

A laboratory scale spray dryer (BUCHI model B-290 Advanced) was used to process the above mentioned feed solution. In Trial #1, the BUCHI unit was equipped with a single two-fluid nozzle where nozzle cap and diameter were 1.4 and 0.7 mm, respectively. In Trial #2, the BUCHI unit was equipped with a duo of two-fluid nozzles (FIG. 6), each one with a nozzle cap and diameter of 1.4 and 0.7 mm (that is, identical to the nozzle of Trial #1).

During the first trial, the flowrate of solution fed to the single nozzle was approximately 3 g/min and the flowrate of atomization gas fed to the single nozzle was approximately 9 g/min (equivalent to 30 mm in the rotameter).

During the second trial, the flowrate of solution fed to the apparatus (duo of nozzles) was 6 g/min and the flowrate of atomization gas fed to the apparatus as approximately 20 g/min (equivalent to 60 mm in the rotameter).

Based on the above conditions, each nozzle (independently of the trial) was being used under similar atomization conditions (atomization ratio=F_atomiz/F_feed approximately 3).

The thermal profile imposed in both tests (that it, the relationship between T_in and T_out) was similar (since significantly different thermal profiles may impact particle formation); the small differences derive from the fact that, in Trial #2, twice the solvent was being evaporated at the same drying gas flowrate, therefore requiring a slightly higher inlet temperature (in order to fulfill the thermodynamic balance).

| Trial | | Single 2-fluid nozzle | Duo of 2-fluid nozzles |
|---|---|---|---|
| F_drying | kg/h | approx. 40 | approx. 40 |
| F_feed | g/min | approx.. 3 | approx. 3 (in each) |
| R_atomiz | | approx. 3 | approx. 3 (in each) |
| T_in | ° C. | 141 | 160 |
| T_out | ° C. | 95 | 95 |
| Yield | % w/w | 86 | 87 |

Note:
F_drying—drying gas flowrate;
F_feed—solution flowrate;
R_atomiz—atomization ratio;
T_in—inlet drying temperature;
T_out—outlet drying temperature.

As can be seen in FIGS. 7 (Single nozzle) and 8 (Duo of nozzles), the particle size distribution and morphology is identical when comparing the powders obtained via the "Single nozzle" and the "Duo of nozzles", demonstrating the success of the current proof-of-concept and, in this way, the feasibility of a multi-nozzle concept, capable of fulfilling all the previous aims and goals.

Example 2

This example demonstrates the proof-of-concept, by considering a multi-nozzle atomizer (shown in FIG. 1) of the invention employed in a SD1 unit.

A feed mixture was prepared by dissolving 1.225 kg of leucine and 4.9 kg of trehalose in 33.8 kg of ethanol and in 135.1 kg of water (total solids concentration approximately 3.5% w/w).

A SD1, operating at a nominal drying gas flow rate of approximately 110 kg/h, was used to process the above mentioned feed solution. In Trial #1, the SD1 unit was equipped with a multi-nozzle atomizer operating with 2 NIRO ETFN (orifice=0.5 mm) and a special housing for homogeneous liquid and gas distribution. In Trial #2, the SD1 unit was equipped with the multi-nozzle atomizer operating with 1 NIRO ETFN (orifice=0.5 mm).

During the first trial, the flowrate of solution fed to the two nozzles of the multi-nozzle atomizer was approximately 2 kg/h and the flowrate of atomization gas fed to the apparatus was approximately 20 kg/h.

During the second trial, the flowrate of solution fed to the single nozzle of the multi-nozzle atomizer was 1 kg/h and the flowrate of atomization gas fed to the apparatus was approximately 10 kg/h.

Based on the above conditions, each nozzle (independently of the trial) was being used under similar atomization conditions (atomization ratio=F_atomiz/F_feed approximately 10).

The thermal profile imposed in both tests (that is, the relationship between T_in and T_out) presented differences that derive from the fact that, in Trial #1, twice the solvent was being evaporated at the same drying gas flowrate, therefore requiring a higher inlet temperature (in order to fulfill the thermodynamic balance).

| Trial | | Multi-nozzle operating with 2 nozzle | Multi-nozzle operating with 1 nozzle |
|---|---|---|---|
| F_drying | kg/h | approx. 110 | approx. 110 |
| F_feed | kg/h | approx. 2 | approx. 1 |
| R_atomiz | | approx. 10 | approx. 10 |
| T_in | ° C. | 151 | 127 |
| T_out | ° C. | 80 | 80 |
| Yield | % w/w | 68 | 64 |

As can be seen in FIGS. 9 and 10 the morphology and particle size distribution is identical when comparing the powders, demonstrating the success of the current proof-of-concept and, in this way, the feasibility of a multi-nozzle concept, capable of fulfilling all the previous aims and goals.

Example 3

This example demonstrates the proof-of-concept, by considering a multi-nozzle atomizer (shown in FIG. 1) of the invention employed in a commercial scale spray dryer unit.

A feed mixture was prepared by dissolving 1.225 kg of leucine and 4.9 kg of trehalose in 33.8 kg of ethanol and in 135.1 kg of water (total solids concentration approximately 3.5% w/w).

A SD2, operating at a nominal drying gas flow rate of approximately 360 kg/h, was used to process the above mentioned feed solution. The SD2 unit was equipped with a multi-nozzle atomizer operating with 4 NIRO ETFN (orifice=0.5 mm) and a special housing for homogeneous liquid and gas distribution.

During the trial, the flowrate of solution fed to the multi-nozzle atomizer was approximately 8 kg/h and the flowrate of atomization gas fed to the apparatus was approximately 20 kg/h.

| Trial | | Multi-nozzle operating with 4 nozzles |
|---|---|---|
| F_drying | kg/h | approx. 360 |
| F_feed | kg/h | approx. 8 |
| R_atomiz | | approx. 2.5 |
| T_in | ° C. | 134 |
| T_out | ° C. | 95 |
| Yield | % w/w | 93 |

As can be seen in FIG. 11 (Multi-nozzle atomizer operating with 4 nozzles), the particle size distribution and morphology is identical to the powders generated in Example 2, demonstrating the success of the current proof-of-concept and, in this way, the feasibility of a multi-nozzle concept, capable of fulfilling all the previous aims and goals.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

What is claimed is:

1. A method for scaling-up a spray drying process for preparing particles for inhalation from a smaller scale spray dryer to a larger scale spray dryer, relative in size to each other, said method comprising the use in the larger scale spray dryer of a multi-nozzle apparatus comprising single nozzles suitable for use in preparing inhalation powders, wherein the smaller scale spray dryer comprises a number m of nozzles and the larger scale spray dryer comprises a number n of nozzles, and wherein n is determined by scaling m by a ratio, which may be rounded up or down to a whole number, of the drying gas flow rate of the larger scale spray dryer to the drying gas flow rate of the smaller scale spray dryer.

2. The method according to claim 1, wherein n is equal to the ratio of the drying gas flow rate of the larger scale spray dryer to the drying gas flow rate of the smaller scale spray dryer rounded up or down to a whole number.

3. The method according to claim 2, wherein the drying gas flow rate of the smaller scale spray dryer is from about 20 kg/h to about 120 kg/h.

4. The method according to claim 3, wherein the drying gas flow rate of the larger spray dryer is greater than about 80 kg/h.

5. The method according to claim 3, wherein the drying gas flow rate of the larger spray dryer is about 360 kg/h, about 650 kg/h, or about 1250 kg/h.

6. The method according to claim 1, wherein m is between 1 and 4.

7. The method according to claim 6, wherein n is between 2 and 16.

8. The method according to claim 1, wherein the drying gas flow rate of the smaller scale spray dryer is about 80 kg/h and the drying gas flow rate of the larger spray dryer is about 360 kg/h and m=1 and n=4 or the drying gas flow rate of the larger spray dryer is about 650 kg/h and m=1 and n=8.

9. The method according to claim 1, wherein the particles for inhalation comprise active pharmaceutical ingredients, drug product intermediates or drug products, optionally organic active pharmaceutical ingredients, drug product intermediates or drug products.

10. The method according to claim 1, wherein the particles have a mean particle size less than about 5 microns.

11. The method according to claim 1, wherein the single nozzles are two-fluid external or internal mixture nozzles.

12. The method according to claim 1, wherein the liquid feed flow and atomization gas flow are homogeneously distributed amongst the single nozzles.

13. The method according to claim 1, wherein all the single nozzles are of the same type.

14. The method according to claim 2, wherein the drying gas flow rate of the smaller scale spray dryer is from about 40 kg/h to about 80 kg/h.

15. The method according to claim 2, wherein the drying gas flow rate of the smaller scale spray dryer is about 40 kg/h.

16. The method according to claim 15, wherein the drying gas flow rate of the larger spray dryer is greater than about 120 kg/h.

17. The method according to claim 16, wherein the drying gas flow rate of the larger spray dryer is greater than 150 kg/h.

18. The method according to claim 15, wherein the drying gas flow rate of the larger spray dryer is about 360 kg/h, about 650 kg/h, or about 1250 kg/h.

19. The method according to claim 16, wherein the drying gas flow rate of the larger spray dryer is about 360 kg/h, about 650 kg/h, or about 1250 kg/h.

20. The method according to claim 1, wherein m=1 or 2 or 3 and n=2 or 3 or 4 or 5 or 8 or 10 or 16.

* * * * *